United States Patent
Boutet

(10) Patent No.: US 7,544,955 B2
(45) Date of Patent: Jun. 9, 2009

(54) SYSTEM FOR SYNCHRONOUS DETECTION OF FLUORESCENCE IN A DROP

(75) Inventor: Jerome Boutet, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 317 days.

(21) Appl. No.: 11/630,993

(22) PCT Filed: Jun. 29, 2005

(86) PCT No.: PCT/FR2005/050515

§ 371 (c)(1),
(2), (4) Date: Dec. 28, 2006

(87) PCT Pub. No.: WO2006/005880

PCT Pub. Date: Jan. 19, 2006

(65) Prior Publication Data

US 2008/0290294 A1    Nov. 27, 2008

(30) Foreign Application Priority Data

Jul. 1, 2004   (FR) .................................. 04 51402

(51) Int. Cl.
G01J 1/58    (2006.01)
(52) U.S. Cl. .................................. 250/459.1
(58) Field of Classification Search ............... 250/458.1, 250/459.1
See application file for complete search history.

(56) References Cited

U.S. PATENT DOCUMENTS

| | | |
|---|---|---|
| 4,211,487 A | 7/1980 | Morrison et al. |
| 6,043,878 A | 3/2000 | Gratzl et al. |
| 6,338,820 B1 | 1/2002 | Hubbard et al. |
| 7,052,244 B2 | 5/2006 | Fouillet et al. |
| 2002/0143437 A1 | 10/2002 | Handique et al. |
| 2004/0007377 A1 | 1/2004 | Fouillet et al. |
| 2004/0055891 A1 | 3/2004 | Pamula et al. |
| 2005/0048581 A1* | 3/2005 | Chiu et al. .................. 435/7.1 |

FOREIGN PATENT DOCUMENTS

FR   2 841 063   12/2003

OTHER PUBLICATIONS

U.S. Appl. No. 11/630,993, filed Dec. 28, 2006, Boutet.
U.S. Appl. No. 11/916,751, filed Dec. 6, 2007, Sauter-Starace, et al.
U.S. Appl. No. 11/917,857, filed Dec. 17, 2007, Sauter-Starace, et al.
Sung Kwon Cho, et al., "Patricle Separation and Concentration Control for Digital Microfluidic Systems", IEEE, 2003, pp. 686-689.
M. G. Pollack, et al., "Electrowetting-based actuation of droplets for integrated microfluidics", Lab Chip, XP008038786, vol. 2, 2002, pp. 96-101 and end page.
Jean-Christophe Roulet, et al., "Performance of an Integrated Microoptical System for Fluorescence Detection in Microfluidic Systems", Analytical Chemistry, vol. 74, No. 14, Jul. 15, 2002, pp. 3400-3407.
Hong Ren, et al., "Design and Testing of an Interpolating Mixing Architecture for Electrowetting-Based Droplet-on-Chip Chemical Dilution", Department of Electrical and Computer Engineering, Duke University, 4 pages.
Kari T. Hjelt, et al., "High-resolution liquid volume detection in sub-nanoliter reactors", Sensors and Actuators, vol. 83, 2000, pp. 61-66.

* cited by examiner

*Primary Examiner*—David P Porta
*Assistant Examiner*—Marcus H Taningco
(74) *Attorney, Agent, or Firm*—Oblon, Spivak, McClelland, Maier & Neustadt, P.C.

(57) ABSTRACT

A method for producing a modulated optical signal from a droplet of a liquid medium. The method positions a droplet of liquid on a hydrophobic surface, in the path of an optical beam, and modulates the shape of the droplet on this surface, by electrowetting, to modulate the signal obtained after passing the optical beam through the droplet.

17 Claims, 5 Drawing Sheets

SYSTEM FOR SYNCHRONOUS DETECTION OF FLUORESCENCE IN A DROP

TECHNICAL FIELD AND STATE OF THE PRIOR ART

The invention concerns techniques for measuring fluorescence in small quantities of liquid, and particularly in droplets of liquid.

Measuring fluorescence consists in exciting fluorescent markers in a liquid, by means of a light source of a predetermined wavelength.

The signal re-emitted by the markers is measured at another wavelength (higher than the excitation wavelength) by means of a detector.

A difficulty arises when one seeks to measure very low concentrations of markers. These fluorescent markers may be either fluorescent molecules, or quantum dots.

In this case, one has to detect a small quantity of fluoropohores in an often considerable background noise stemming, for example, from the fluorescence of the support of the sample measured, or dust or surrounding optical means, such as the optics of a microscope for example.

As illustrated in FIG. 1A, a fluorescence measurement chain generally associates a sensor 2, which recovers a fluorescence light beam 4, an amplifier 6 and a filtering system 8 that attenuates the noise.

The output voltage of the amplifier 8 is of the type:

$$V\text{out}=G \times S+b(t),$$

Where:
G=gain of the amplifier
S=physical variable measured
b(t)=noise

Thus, the filter 8 is going to enable the useful signal to be recovered and the presence of noise b(t) to be minimised.

Since the phenomenon studied generally has slow variations, it therefore involves, most of the time, a low pass filtering.

The filtering may be obtained electronically or by integrating the signal over a certain period (case of CCD sensors) or even by averaging over several images.

FIG. 1B represents a signal S after selective amplification by the amplifier 60, and the spectral shape F of the low pass filter 80.

The limitation of this type of device is that it does not enable low frequency noise to be eliminated such as, for example, the fluorescence of the substrate, the optics of any microscope, optical filters or even slow thermal fluctuations of the experiment.

One may do with this type of measurement if the signal to noise ratio corresponds to the requirements definition.

If this is not the case, a means of minimising the influence of low frequency noise has to be found.

It is sometimes possible to attenuate the effect of this noise by carrying out differential measurements compared to a negative control, but such a device has a certain number of disadvantages.

Firstly, it imposes size constraints since it is necessary to add a negative control and a supplementary sensor.

It also imposes cost constraints, because the device is more bulky and it therefore necessitates a longer development.

Finally, precision is not always assured because it is not certain that the negative control is exactly under the same thermal or chemical conditions as the positive control.

Synchronous detection enables a signal in a considerable noise to be measured without using negative control or supplementary sensor.

As illustrated in FIG. 2A, a measuring device with synchronous detection comprises, apart from a sensor 20, which recovers a fluorescence light beam 40, an amplifier 6, elements already described above in liaison with FIG. 1, a multiplier 110 and a low pass integrator 120.

Carrying out a synchronous detection measurement consists in varying periodically the physical phenomenon studied, in such a way as to modulate the physical variable measured.

With the modulation, the output signal of the amplifier 6 becomes:

$$V\text{out}=G \times S \times \cos(W_m t)+b(t)$$

Where:
G=gain of the amplifier,
S=physical variable measured,
$W_m$=modulation pulsation ($w_m = 2\pi f_m$),
b(t)=noise.

The choice of the modulation frequency $W_m$ is linked to the frequency zone where the spectral density of the noise is minimal.

The role of the selective filter 12 is going to consist in only conserving at the chain output the modulation frequency $f_m$.

After amplification, by the amplifier 6, the signal is again multiplied by the multiplier 10 by the carrier $\cos(w_m t)$ $$V_{mult}=(G \times S \times \cos(w_m t)+b(t)) \times \cos(w_m t)$$

$$V_{mult}=G \times S/2+(G \times S/2) \times \cos(2w_m t)+b(t) \times \cos(w_m t).$$

The first component (GS/2) is continuous, the second is in $2w_m$ and the third corresponds to the noise and is centered in $w_m$.

After the multiplication, the signal is then filtered by a low pass integrator 12 to only conserve the component proportional to the signal of the sensor: $G \times S/2$.

FIG. 2B represents the signal S after amplification by the amplifier 60, the spectral shape A of the selective amplifier 60, and the shape of the noise b.

FIG. 2C represents the signal after demodulation: the 3 components of $V_{mult}$ are separated; that which is proportional to the signal of the sensor ($G \times S/2$) may be isolated by means of the low pass filter 120 (of spectrum F').

"Classical" synchronous detection is based for example on the modulation of the supply of the sensor or the light source. But it does not enable the fluorescence of the support or the optics to be eliminated because this fluorescence is also modulated.

Practically, the problem is therefore posed of finding a device and a method enabling a synchronous detection to be carried out on droplets or microdroplets of liquid.

Another problem is eliminating, in such a synchronous detection, any parasite fluorescence, while only conserving the signal coming from the droplet.

Preferably, such a method and such devices should enable various types of measurements to be carried out, such as fluorescence or spectrometry (especially absorption) or colorimetry measurements.

DESCRIPTION OF THE INVENTION

The invention concerns a method for producing a modulated optical signal from a droplet of a liquid medium comprising:

the positioning of a droplet of liquid on a hydrophobic surface, in the path of an optical beam, the modulation of the shape of the droplet on this surface, by electrowetting, in order to modulate the signal obtained after passing the optical beam through the droplet.

According to the invention, one uses a method of electrowetting to modulate the shape of the droplet at a defined frequency in order to carry out a synchronous detection of the light signal coming from the droplet and, in particular, to eliminate the background noise.

For example, within the scope of a laboratory on a chip, when the droplet, after a displacement, arrives on the detection zone, one or several electrodes may be activated to modify the shape of the droplet, then deactivated to make it recover its initial form, then activated again and so on.

The shape of the droplet varies therefore periodically over time, as does consequently the profile that the signal presents in the detector.

This detector measures a periodic signal and an instrumentation chain, or means of processing the signal, can analyze the signal coming from this synchronous detection on the measured signal.

The signal from the sensor can therefore be modulated to carry out a synchronous detection of the fluorescence or the absorption or any other optical phenomenon.

The modulation of the droplet may be achieved by means of a two-dimensional matrix or a row of electrodes of identical size.

In this case, it is the activation and the deactivation of the electrodes near to the droplet that modulates the shape of the droplet.

According to another possibility, the modulation may be obtained by a single electrode activated then deactivated, for example an electrode of lengthened shape.

The droplet may also be displaced in front of, then outside, the measurement window. Thus, the detection window receives either the fluorescence of the droplet when this is in front of the window, or the fluorescence of the background noise when the droplet is outside of the window.

This method of synchronous detection in the droplet may apply to any form of optical detection and, in particular, to a measurement in colorimetry, or in spectrometry, or in fluorescence.

The droplet may be confined, at least during its modulation, between the hydrophobic surface and an upper substrate.

The droplet may, before modulation, not be confined by the upper substrate. One is then in the case of a mixed system, which makes the droplet pass from a non confined state to a confined state.

It may also, before modulation, be confined by the upper substrate.

The invention further concerns a method of synchronous detection of an optical signal, comprising the implementation of a method as described above, then a step of demodulation of the optical signal.

The step of demodulation of the optical signal may comprise a multiplication of the modulated signal by a carrier signal at the frequency of modulation and a low pass filtering.

The invention further concerns a device for optically analyzing a droplet of a liquid medium comprising:

a first substrate comprising a hydrophobic surface, means of generating a radiation to generate an optical beam; this is parallel to the hydrophobic surface, in a confined configuration, and may be parallel to said surface or have another direction in the case of an open system, means for modulating the shape of a droplet, on this surface, by electrowetting.

Such a device may further comprise a second substrate, arranged facing the hydrophobic surface.

This second substrate may further comprise a superficial hydrophobic layer and/or an electrode underneath.

The means for modulating the shape of a droplet, on the hydrophobic surface, by electrowetting, may comprise a plurality of electrodes under the hydrophobic surface.

These electrodes may be all of identical size, or instead one at least of the electrodes may be of lengthened shape.

A device for synchronous detection of an optical signal may comprise, apart from a device as described above, means carrying out a demodulation treatment of a synchronous signal.

DETAILED DESCRIPTION OF SPECIFIC EMBODIMENTS

Figure 3A:
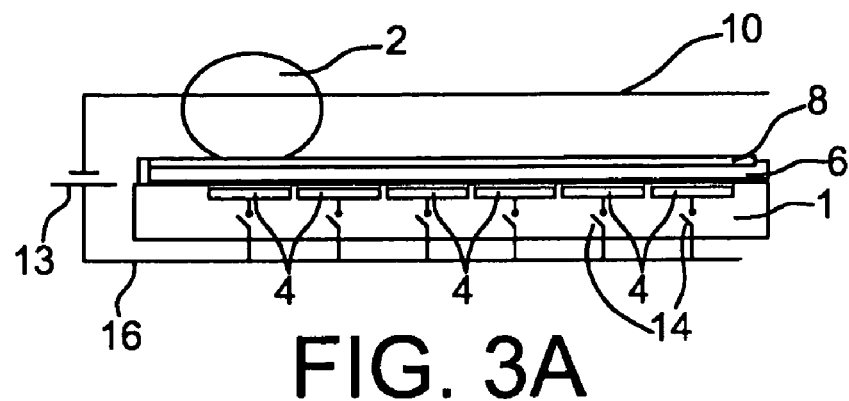
FIGS. 3A-3C represent an embodiment of a device according to the invention, in open system.
Figure 3B:
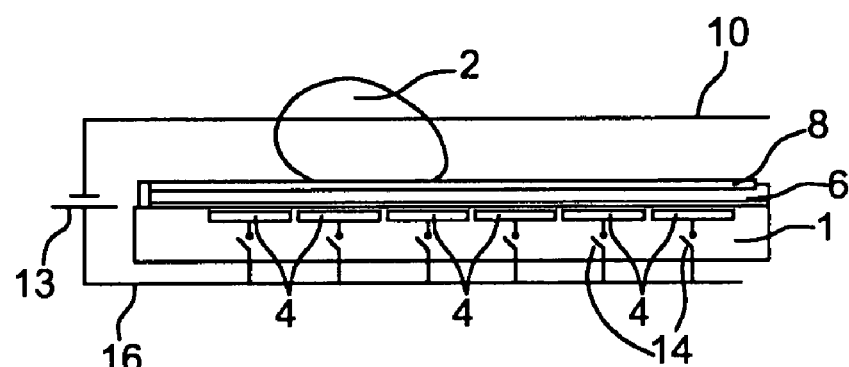
Figure 3C:
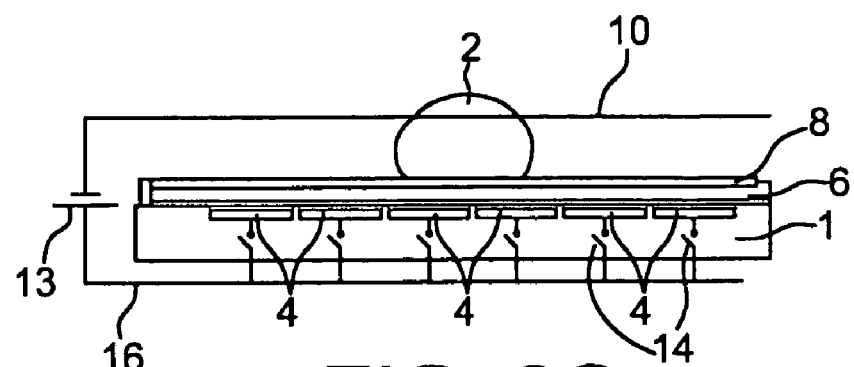

A first embodiment of the invention, in open system, is illustrated in FIGS. 3A-3C.

This embodiment implements a device for displacing or manipulating droplets of liquid based on the principle of electrowetting on a dielectric.

Examples of such devices are described in the article of M. G. Pollack, A. D. Shendorov, R. B. Fair, entitled "Electrowetting-based actuation of droplets for integrated microfluidics", Lab Chip 2 (1) (2002) 96-101.

The forces used for the displacement of droplets of liquid are then electrostatic forces.

The document FR 2 841 063 also describes a device implementing, moreover, a catenary facing the activated electrodes for the displacement as counter electrode.

The principle of this type of displacement is summarized in FIGS. 3A-3C.

A droplet 2 is lying on a network 4 of electrodes, from which it is isolated by a dielectric layer 6 and a hydrophobic layer 8 (FIG. 3A).

The hydrophobic character of this layer signifies that the droplet has a contact angle, on this layer, greater than 90°.

The electrodes are themselves formed on the surface of a substrate 1.

When the electrode 4-1 located near to the droplet 2 is activated, by means of commutation means 14, the closing of which establishes a contact between this electrode and a voltage source 13 via a shared conductor 16, the dielectric layer 6 and the hydrophobic layer 8 between this activated electrode and the droplet, permanently polarized by a counter electrode 10, act as a capacitor. The effects of electrostatic charges induce the displacement of the droplet on the activated electrode. The counter electrode 10 enables the displacement by electrowetting, it maintains an electrical contact with the droplet during its displacement. This counter electrode 10 may be either a catenary as described in FR-2 841 063, or a buried wire, or a planar electrode on or in the cover of confined systems.

In open system, if there is no displacement, it is possible to spread out and modulate a droplet on the hydrophobic surface, without counter electrode. This is for example the case if the droplet may be brought onto the hydrophobic surface by a conventional dispensation system, the electrodes 4-1, 4-2 serving uniquely to spread out or to modulate the droplet at the spot where it has been deposited.

The droplet may thus be displaced if necessary step by step (FIG. 3C), on the hydrophobic surface 8, by successive activation of the electrodes 4-1, 4-2, etc. and along the catenary 10.

It is thereby possible to displace liquids, but also to mix them (by bringing droplets of different liquids together), and to carry out complex protocols.

The documents cited above give examples of implementations of series of adjacent electrodes for the manipulation of a droplet in a plane, the electrodes may indeed be arranged in a linear manner, but also in two dimensions, thereby defining a displacement plane for the droplets.

Figure 4:
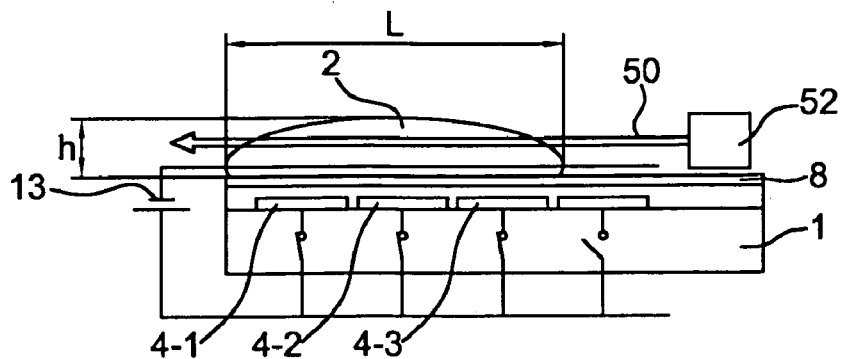
FIG. 4 represents a modulation of a droplet, in the path of an optical beam, in open system.

As illustrated in FIG. 4, the simultaneous activation of several electrodes, designated in this figure by the references 4-1, 4-2, 4-3, is going to make it possible to lengthen the droplet 2 along the desired direction, this direction being in fact determined by the electrodes 4-1, 4-2, 4-3 selected.

Figure 5A:
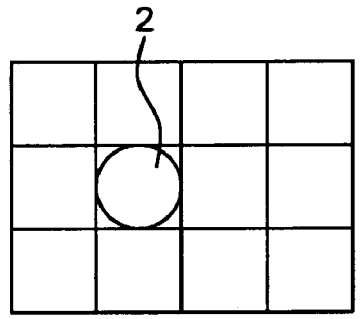
FIGS. 5A and 5B represent top views of a device and a droplet, before and during a measurement according to the invention.
Figure 5B:
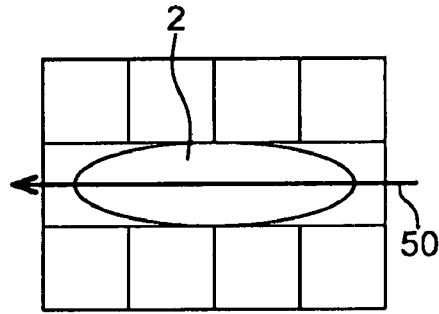

FIGS. 5A and 5B represent a top view of the system, in which the electrodes 4 are shown schematically by squares, the droplet again being designated by the reference 2.

Before activation of the electrodes, the droplet 2 lies on one of them; after activation of the electrodes 4-1, 4-2, 4-3, 4-4, the droplet 2 is stretched out and positioned above these four same electrodes. FIG. 4 represents the case where only three electrodes are selected, stretching the droplet onto these 3 electrodes.

The droplet is then in a state in which its length L (see FIG. 4), measured parallel to the hydrophobic surface 8, is greater than its height h, for example in a L/h ratio of around 2 to 4 or more.

These same electrodes are then deactivated, which makes the droplet regain its initial shape, then again activated, then again deactivated and so on.

A beam 50, of wavelength suited to the desired measurement (with a view to a measurement of absorption or fluorescence or colorimetry or spectrometry) therefore sees its path in the droplet notably increased due to the lengthening of said droplet, then again reduced when said droplet recovers its initial shape, then again increased and so on.

The measurement signal is therefore modulated by modulation of the shape of the droplet itself. This is particularly advantageous when the volume of liquid examined is around, at the maximum, several microlitres, and can even attain very low values, for example around a nanolitre.

In a practical manner, one will position light emitting means 52, in such a way as to direct a beam 50 along the substrate.

A detector 54 will detect the modulated signal.

The activation of the electrodes 4 will make it possible, firstly if necessary to displace or position, then to modulate the shape of the droplet 2 along the beam 50, as explained above, and thereby to modulate the corresponding measured signal.

Therefore successions of activation—deactivation of the electrodes 4 are performed in order to modulate the signal as explained above.

The modulation may take place at a frequency between, for example, 10 Hz and 100 Hz.

Figure 6:
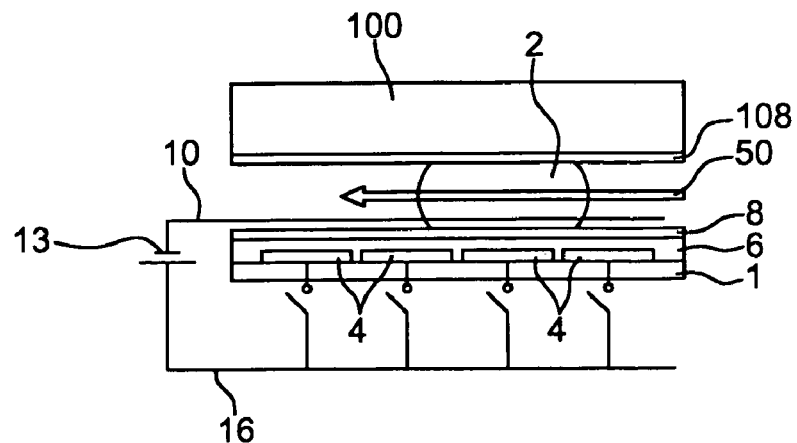
FIG. 6 represents a device implemented within the scope of the invention, in closed system.

FIG. 6 represents another embodiment of the invention, in closed system.

In this figure, numerical references identical to those of FIGS. 3A-4 designate identical or corresponding elements.

This device further comprises an upper substrate 100, preferably also covered with a hydrophobic layer 108. This assembly may if necessary be transparent, enabling an observation from above.

Here again, a light beam may be directed between the two substrates.

In a practical manner, one will position light emitting means, analogous to the means 52 of FIG. 5, in such a way as to direct a beam 50 along the substrate.

The activation then the deactivation of the electrodes 4 of the lower substrate make it possible, firstly if necessary to displace or position, then to modulate the shape of the droplet 2 along the beam 50.

Figure 7A:
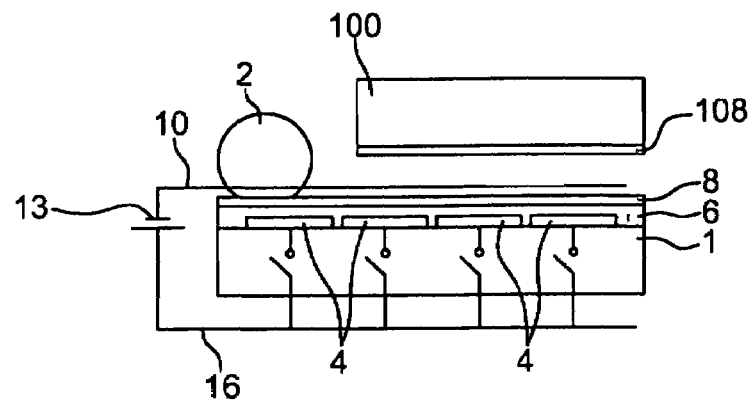
FIGS. 7A and 7B represent an implementation of the invention, in mixed open and closed system.
Figure 7B:
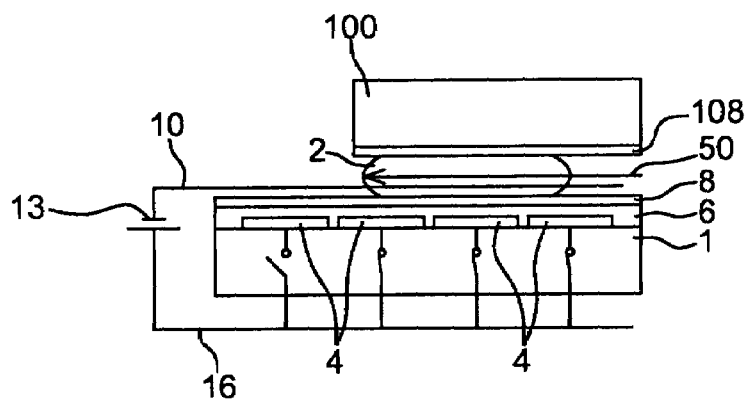

FIGS. 7A and 7B represent a system in which a droplet 2 is initially in open medium, the selective activation of electrodes 4 enabling an alignment and a modulation of the droplet, in closed system, in a zone where the system is provided with a cover 100, as illustrated above in liaison with FIG. 4.

Figure 8:
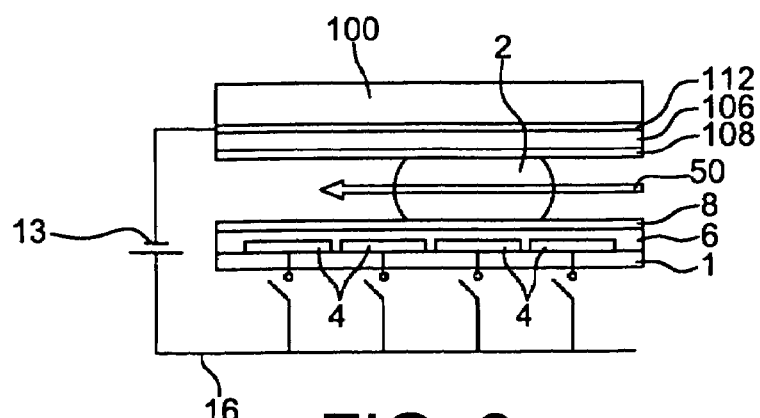
FIG. 8 represents a device implemented within the scope of the invention, in closed system with conductor cover.

FIG. 8 represents an alternative embodiment of the closed system, with a conductor cover 100, comprising an electrode or a network of electrodes 112, and an insulator layer 106 if necessary and a hydrophobic layer 108.

The catenary 10 of the previous figures is replaced, in this embodiment, by the electrode 112. The activation of this electrode and the repeated activation then the deactivation of the electrodes 4 makes it possible to displace the droplet 2 to the desired position then to modulate its shape as already explained above.

Figure 9A:
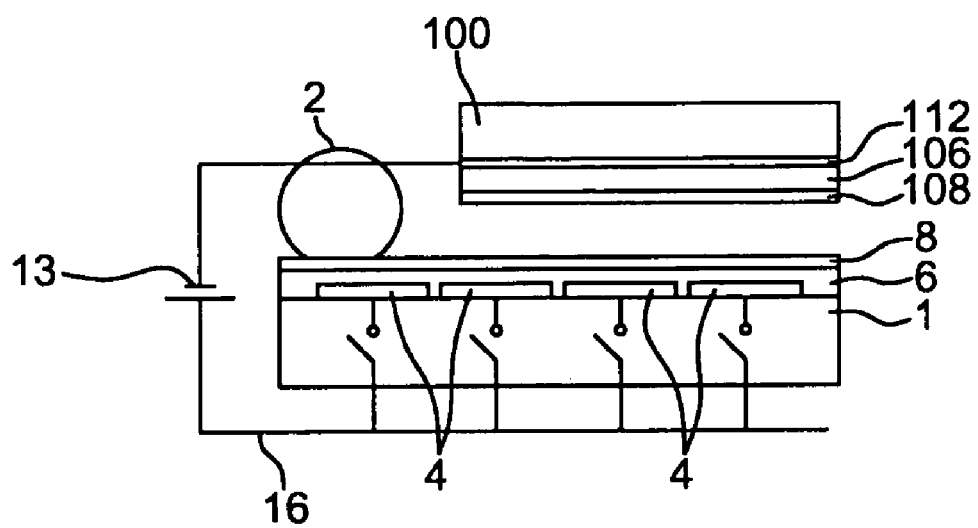
FIGS. 9A and 9B represent a device implemented within the scope of the invention, in mixed system with conductor cover.
Figure 9B:
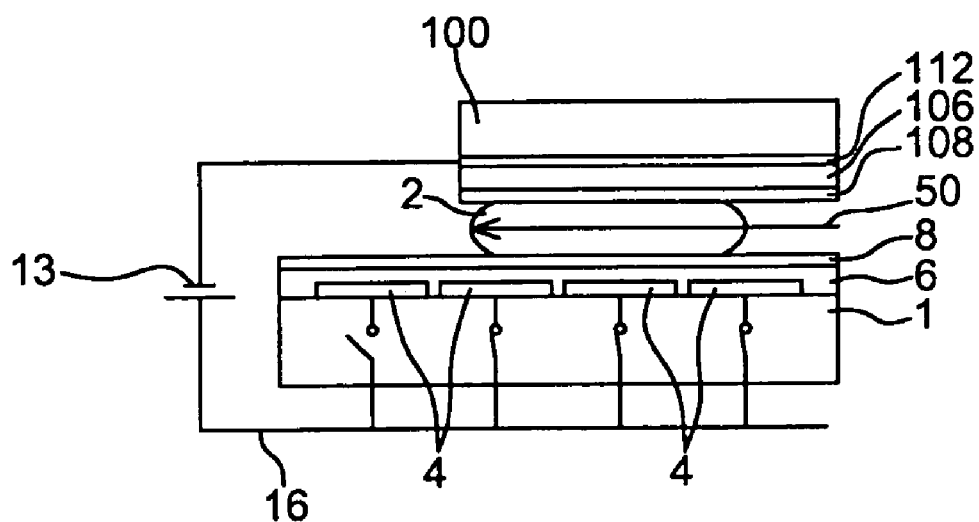

FIGS. 9A and 9B, in which numerical references identical to those of FIG. 8 designate identical or similar elements, represents a mixed system, in which a droplet 2 is initially in open medium (FIG. 8A), the selective activation of the electrodes 4 enabling a modulation of the shape of the droplet (FIG. 9B), in closed system, in a zone where the system is provided with a cover 100, as illustrated above in liaison with FIG. 8.

In the embodiments described above, several electrodes 4 are activated to deform and modulate the droplet. It is also possible to provide for an electrode of lengthened shape, the activation of which would enable the droplet to be flattened, again by electrowetting effect. The deactivation of this electrode would bring back the droplet to its initial shape. The droplet may then again be deformed and so on, thus achieving, once again, a modulation of the shape of the droplet in the path of the light beam 50, and thereby a modulation of the measured signal, whatever the nature of the measurement (absorption, fluorescence, transmission etc.).

The electrodes 4 receive an electric voltage, a voltage that may be amplified. The activation or the deactivation may take place via a relay or via an analogical, or digital, multiplexer, or a logic gate. The activation of the electrodes may be managed by computer or PC type digital means controlling relays such as the relays 14 of FIG. 3A.

Typically, the distance between any conductor 10 (FIGS. 3A-7B) on the one hand and the hydrophobic surface 8 on the other hand is, for example, between 1 µm and 100 µm or 500 µm.

The conductor 10 is, for example, in the form of a wire of diameter between 10 µm and several hundreds of µm, for example 200 µm. This wire may be a wire of gold or aluminum or tungsten or other conductive materials.

When two substrates 1, 100 are used (FIGS. 8-9B), they are separated from each other by a distance of between, for example, 10 µm and 100 µm or 500 µm.

Whatever the embodiment considered, a droplet of liquid 2 will have a volume between, for example, 1 nanolitre and several microlitres, for example between 1 nl and 5 µl or 10 µl.

Moreover, each of the electrodes 4 will have for example a surface area of around several tens of µm2 (for example 10 µm2) up to 1 mm2, depending on the size of the droplets to be transported, the spacing between neighboring electrodes being for example between 1 µm and 10 µm.

The structuring of the electrodes 4 may be obtained by conventional microtechnology methods, for example by photolithography. The electrodes are for example formed by deposition of a metallic layer (Au, or Al, or ITO, or Pt, or Cr, or Cu, etc.) by photolithography. The substrate is then covered with a dielectric layer in $SiN_4$, or $SiO_2$, etc. Finally, a deposition of a hydrophobic layer is carried out such as, for example, a deposition of Teflon carried out by a spin coater.

Methods for forming chips incorporating a device according to the invention may be derived directly from the methods described in the document FR-2 841 063.

Conductors, and in particular buried conductors 112, may be formed by deposition of a conductive layer and etching of this layer following the appropriate pattern of conductors, before deposition of the hydrophobic layer 108.

The substrates 1, 100 are for example in silicon, or glass, or plastic.

Figure 1A:
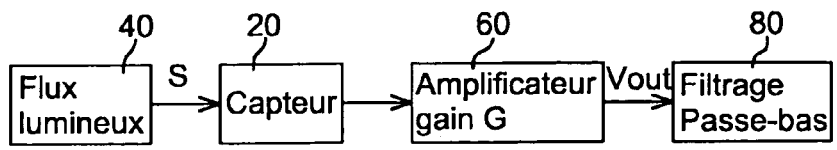
FIGS. 1A to 2C represent known techniques and shapes of signals before and after treatment by these known techniques.
Figure 1B:
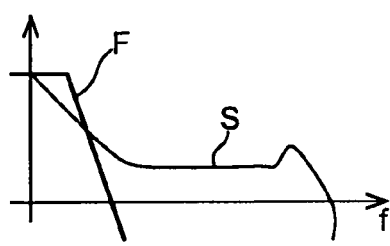
Figure 2A:
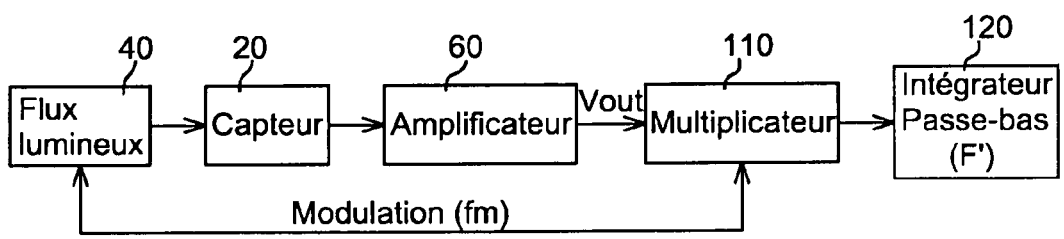
Figure 2B:
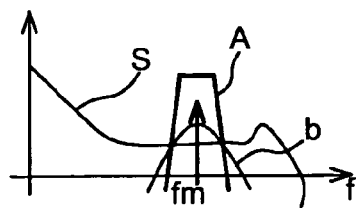
Figure 2C:
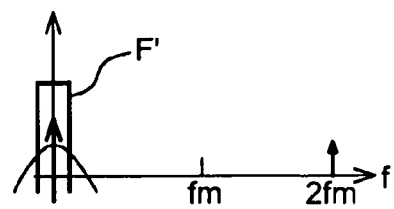

Once a modulated signal conforming to the invention has been obtained, this signal may be amplified, multiplied by the modulation function at the frequency fm, function that is known, then integrated as already explained in liaison with FIGS. 2A-2C.

A device according to the invention may therefore comprise, moreover, means of synchronous detection: amplifier means 60, a multiplier 110, a low pass integrator 120 as illustrated in FIG. 2A.

The applied treatment will be that explained above in liaison with FIGS. 2B-2C: a demodulation of the optical signal, comprising a multiplication of the modulated signal by a carrier signal at the frequency of modulation and a low pass filtering.

The invention therefore concerns a method of synchronous detection of an optical signal, comprising the implementation of a method as described above, in order to acquire a modulated optical signal, then a step of demodulation of the optical signal.

The invention has in particular the following advantages:
it improves the signal to noise ratio compared to a conventional measurement. It is particularly suited to the measurement of signals comprising low frequency noise (thermal, etc.),
compared to a differential measurement, the invention does not require negative control or supplementary sensor,
the modulation is carried out by the electrowetting device itself and does not necessitate any additional component. "Classical" synchronous detection (modulation of the light source, for example), does not enable the fluorescence of the support and the optics to be eliminated because this fluorescence itself is also modulated. The system proposed by the invention only modulates the droplet, and therefore enables any parasite fluorescence to be eliminated and only conserves that which comes from the droplet.

The invention claimed is:

1. A method of optically analyzing a droplet of a liquid medium, comprising:
    forming a modulated optical signal coming from a droplet of a liquid medium by:
        positioning a droplet of liquid on a hydrophobic surface, in the path of an optical beam,
        modulating the shape of the droplet on the hydrophobic surface, by electrowetting, to modulate the signal obtained after passing the optical beam through the droplet, and
        then demodulating the signal obtained on exiting the droplet.

2. A method according to claim 1, the droplet being confined, at least during the modulating, between the hydrophobic surface and an upper substrate.

3. A method according to claim 2, the droplet not being, before the modulating, confined by the upper substrate.

4. A method according to claim 2, the droplet being, before the modulating, confined by the upper substrate.

5. A method according to claim 1, further comprising displacing the droplet on the hydrophobic surface.

6. A method according to claim 1, the modulating being obtained by activation of a plurality of electrodes, located underneath the hydrophobic layer.

7. A method according to claim 1, the modulating being obtained by activation of a single electrode, located underneath the hydrophobic layer.

8. A method according to claim 1, the optical analysis being an analysis by colorimetry, or by spectrometry, or by fluorescence.

9. A method according to claim 1, comprising implementing an electrowetting device, including a first substrate covered with the hydrophobic layer, and a plurality of electrodes arranged under the hydrophobic layer.

10. A method according to claim 1, the demodulating optical signal comprising multiplying of the modulated signal by a carrier signal at a frequency of modulation and a low pass filtering.

11. A device for optically analyzing a droplet of a liquid medium comprising:
    a first substrate including a hydrophobic surface;
    means for generating a radiation to generate an optical beam parallel to the hydrophobic surface;
    means for modulating the shape of a droplet, on the hydrophobic surface, by electrowetting; and
    means for carrying out a demodulation treatment of an optical signal.

12. A device according to claim 11, further comprising a second substrate, arranged facing the hydrophobic surface.

13. A device according to claim 9, the second substrate including a superficial hydrophobic layer.

14. A device according to claim 12, the second substrate further including an electrode.

15. A device according to claim 11, the means for modulating the shape of a droplet, on the hydrophobic surface, by electrowetting, including a plurality of electrodes under the hydrophobic surface.

16. A device according to claim 15, the electrodes all being of identical size.

17. A device according to claim 15, at least one of the electrodes being of lengthened shape.

* * * * *